United States Patent
Labron et al.

(10) Patent No.: US 10,885,709 B2
(45) Date of Patent: Jan. 5, 2021

(54) VIRTUAL REALITY SOFTWARE SYSTEM AND METHOD FOR TREATING MEDICAL CONDITION IN USER

(71) Applicants: Robert Labron, Paris (CA); Kimberley Clark-White, Paris (CA)

(72) Inventors: Robert Labron, Paris (CA); Kimberley Clark-White, Paris (CA)

( * ) Notice: Subject to any disclaimer, the term of this patent is extended or adjusted under 35 U.S.C. 154(b) by 0 days.

(21) Appl. No.: 16/008,981

(22) Filed: Jun. 14, 2018

(65) Prior Publication Data
US 2019/0385367 A1    Dec. 19, 2019

(51) Int. Cl.
*G06T 19/00*    (2011.01)
*A61B 5/00*    (2006.01)
*G06F 3/0481*    (2013.01)

(52) U.S. Cl.
CPC ............ *G06T 19/003* (2013.01); *A61B 5/744* (2013.01); *A61B 5/749* (2013.01); *G06F 3/04815* (2013.01); *G06T 19/006* (2013.01)

(58) Field of Classification Search
None
See application file for complete search history.

(56) References Cited

U.S. PATENT DOCUMENTS

| | | | |
|---|---|---|---|
| 5,546,943 A | 8/1996 | Gould | |
| 5,678,571 A | 10/1997 | Brown | |
| 6,186,145 B1 | 2/2001 | Brown | |
| 6,425,764 B1 | 7/2002 | Lamson | |
| 6,918,769 B2 * | 7/2005 | Rink | G16H 20/00 434/247 |
| 9,694,155 B2 | 7/2017 | Stoianova et al. | |
| 9,814,423 B2 | 11/2017 | Jain et al. | |
| 2004/0121295 A1 | 6/2004 | Stuart et al. | |
| 2004/0212152 A1 * | 10/2004 | Kaplan | A63F 13/80 273/429 |
| 2011/0213197 A1 * | 9/2011 | Robertson | A61B 5/486 600/27 |
| 2012/0277594 A1 * | 11/2012 | Pryor | G06F 3/017 600/476 |
| 2014/0316192 A1 * | 10/2014 | de Zambotti | A61B 5/0205 600/28 |
| 2015/0306340 A1 * | 10/2015 | Giap | A61B 6/03 600/301 |
| 2016/0086500 A1 * | 3/2016 | Kaleal, III | G06F 19/3481 434/257 |
| 2017/0287225 A1 * | 10/2017 | Powderly | G06T 19/006 |
| 2018/0154106 A1 * | 6/2018 | S Nchez Vives | A61M 21/02 |

(Continued)

FOREIGN PATENT DOCUMENTS

| | | |
|---|---|---|
| WO | 2007016241 | 2/2007 |
| WO | 2014124002 | 8/2014 |
| WO | 2017087567 A1 | 5/2017 |

*Primary Examiner* — Hilina K Demeter
(74) *Attorney, Agent, or Firm* — Argus Intellectual Enterprise; Jordan Sworen; Daniel Enea

(57) ABSTRACT

A virtual reality software system including a virtual reality headset with a display unit configured to display a three-dimensional virtual reality environment. The virtual reality headset includes a processor and a memory to display the three-dimensional virtual reality environment on the display unit. The virtual reality software system is useful for providing a simulation for completing a medical-mission to eliminate a virtual-representation of a medical condition associated with a user.

18 Claims, 5 Drawing Sheets

(56) References Cited

U.S. PATENT DOCUMENTS

2018/0232050 A1* 8/2018 Ofek .................. G06T 3/0093
2018/0256258 A1* 9/2018 Nash .................. A61B 34/25
2018/0261332 A1* 9/2018 Baeuerle ............. G16H 50/50
2019/0318640 A1* 10/2019 Goel .................. G02B 27/017

* cited by examiner

VIRTUAL REALITY SOFTWARE SYSTEM AND METHOD FOR TREATING MEDICAL CONDITION IN USER

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of treatments for medical conditions of existing art and more specifically relates to a virtual reality software for psychologically treating a medical condition.

RELATED ART

Being diagnosed with a medical condition such as diabetes, cancer or heart disease can be difficult to cope with. It's normal to experience a range of emotions in the wake of such a diagnosis. Distress is common following a diagnosis of a medical condition. In the past, patients have been guided to practice a variety of techniques such as yoga, counseling, behavior medications and the like to deal with the emotions associated with a medical condition. However, facing the medical condition head-on may lead to the best way of coping. Therefore, a suitable solution is desired.

U.S. Pat. No. 6,186,145 to Stephen J. Brown relates to a method for diagnosis and treatment of psychological and emotional conditions using a microprocessor-based virtual reality simulator. The described method for diagnosis and treatment of psychological and emotional conditions using a microprocessor-based virtual reality simulator includes methods and systems for monitoring, diagnosing and/or treating psychological conditions and/or disorders in patients with the aid of computer-based virtual reality simulations. Pursuant to one preferred embodiment, a computer program product is used to control a computer. The program product includes a computer-readable medium, and a controlling mechanism that directs the computer to generate an output signal for controlling a video display device. The video display device is equipped to display representations of three-dimensional images, and the output signal represents a virtual reality simulation directed to diagnosis and/or treatment of a psychological condition and/or disorder.

SUMMARY OF THE INVENTION

In view of the foregoing disadvantages inherent in the known treatments for medical conditions art, the present disclosure provides a novel virtual reality software system and method. The general purpose of the present disclosure, which will be described subsequently in greater detail, is to provide an efficient and effective virtual reality software system and method.

A virtual reality software system is disclosed herein. The virtual reality software system includes a virtual reality headset having a display unit configured to display a three-dimensional virtual reality environment. The virtual reality headset may include a processor embedded in the virtual reality headset and configured to provide controls for performing one or more multimedia interactions with the three-dimensional virtual reality environment. The virtual reality headset may further include a memory removably embedded in the virtual reality headset and configured to store the multimedia interactions.

The processor of the virtual reality headset may further be configured to communicate with the memory, to execute said multimedia interactions, and to display the multimedia interactions on the display unit such that the user is able interact with the three-dimensional virtual reality environment.

The virtual reality headset may be configured to host a software providing the three-dimensional virtual reality environment. The three-dimensional virtual reality environment is configured to provide a simulation for completing a medical-mission to eliminate a virtual-representation of a medical condition associated with the user. This may enable the user to psychologically treat and face the medical condition by obtaining the virtual-representation of their medical condition.

According to another embodiment, a method for using a virtual reality software system is also disclosed herein. The method for using the virtual reality software system includes providing a virtual reality software system as described above; interacting with the three-dimensional virtual reality environment with an avatar; controlling the avatar via a controller in communication with the virtual reality headset; and completing the medical-mission with the avatar to provide therapeutic relief to the user for the medical-condition.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a virtual reality software system and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to treatments for medical conditions and more particularly to a virtual reality software system and method as used to improve the emotional and psychological reactions and consequences of being diagnosed with a medical condition.

Generally, the present disclosure provides an interactive software or "video game" where users can battle their personalized medical condition or illness to mentally improve wellbeing. The software may allow the user to travel throughout the human anatomy to reach the location of their specific medical condition or illness and attack it. By doing so, the user may mentally heal themselves and increase positive reinforcement for fighting the medical condition. The present disclosure may substantially benefit to users during long wait times for appointments and those who are admitted to hospital for lengthy treatments.

Referring now more specifically to the drawings by numerals of reference, there is shown in FIGS. 1-4, various views of a virtual reality software system 100.

Figure 1:
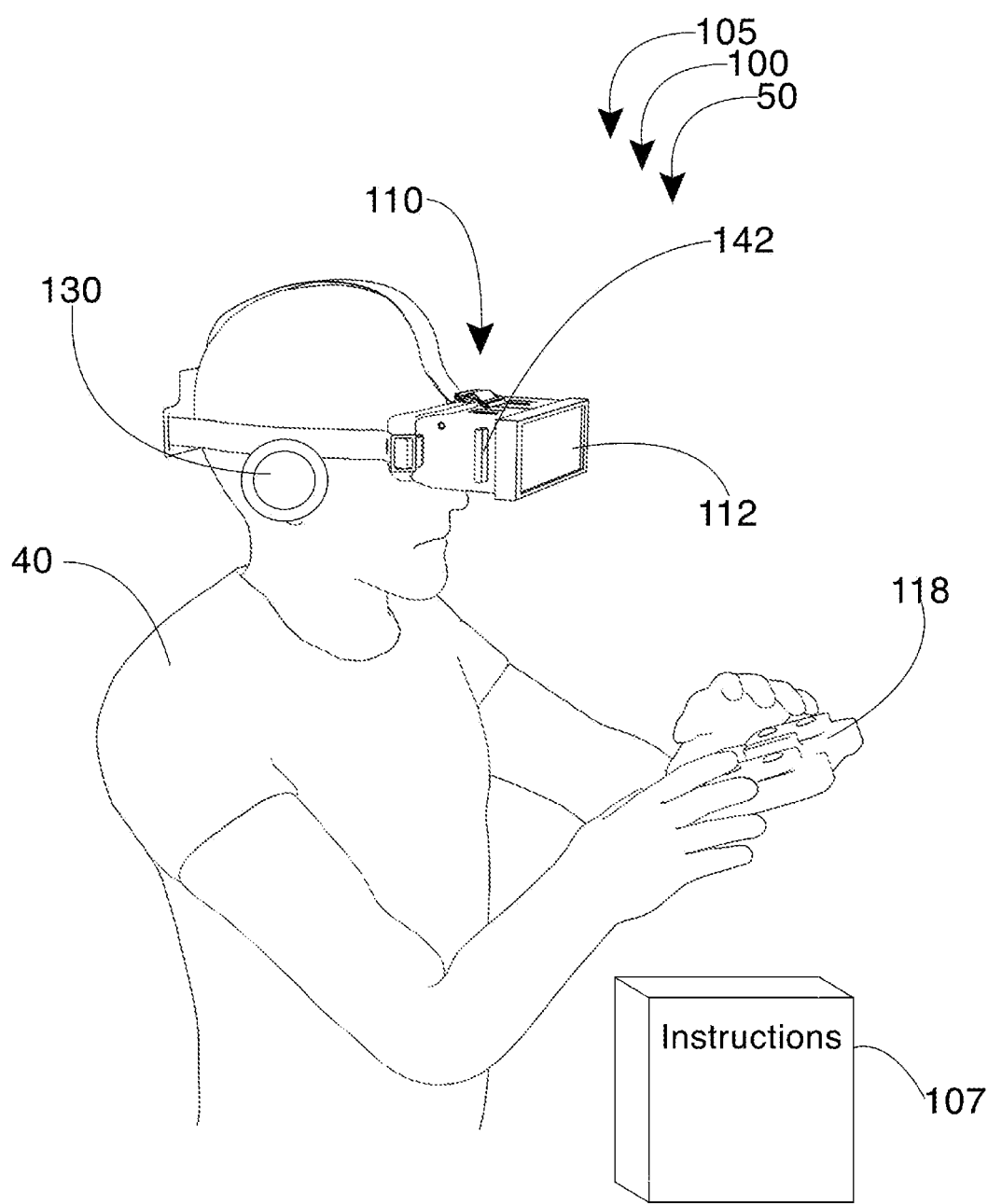
FIG. 1 is a perspective view of the virtual reality software system during an 'in-use' condition, according to an embodiment of the disclosure.

FIG. 1 shows a virtual reality software system 100 during an 'in-use' condition 50, according to an embodiment of the present disclosure. Here, the virtual reality software system 100 may be beneficial for use by a user 40 to treat the mental and emotional state of the user 40 associated with a medical condition via a simulation. As illustrated, the virtual reality software system 100 may include a virtual reality headset 110 having a display unit 112 (head mounted display) configured to display a three-dimensional virtual reality environment 120. The virtual reality headset 110 includes a processor 114 embedded within. The processor 114 may be configured to provide controls for performing one or more multimedia interactions 124 with the three-dimensional virtual reality environment 120. Multimedia interactions 124 may be understood as virtual interactions performed by the user within the three-dimensional virtual reality environment 120 (i.e., shooting, flying, right turn, left turn, aiming, etc.).

The virtual reality headset 110 further includes a memory 116 removably embedded within. The memory 116 may be configured to store the multimedia interactions 124 made within the three-dimensional virtual reality environment 120. The memory 116 may further be configured to store a software 150. The memory 116 may include a removable hardware 140, such as a flash memory card. A port 142 may be included on the virtual reality headset 110 for receiving the removeable hardware 140.

The processor 114 may further be configured to communicate with the memory 116; execute the multimedia interactions 124; and display the multimedia interactions 124 on the display unit 112 such that the user 40 is able to interact with the three-dimensional virtual reality environment 120.

A controller 118 in communication with the virtual reality headset 110 may be provided to the user 40 for performing the multimedia interactions 124 within the three-dimensional virtual environment 120. In an alternate embodiment, the virtual reality headset 110 may include a microphone (not shown) to provide a voice recognition system permitting the user 40 to perform the multimedia interactions 124 with the three-dimensional virtual environment 120. The voice recognition system may provide an output of synthesized voice instructions and be configured to receive an input of voice commands from the user via the microphone.

The virtual reality headset 110 may be configured to host the software 150 providing the three-dimensional virtual reality environment 120. The three-dimensional virtual reality environment 120 may be configured to provide a simulation for completing a medical-mission to eliminate a virtual-representation of a medical condition associated with the user 40. The medical-mission can be utilized to emotionally and mentally treat the user 40 by destroying the visual virtual-representations.

According to one embodiment, the virtual reality software system 100 may be arranged as a kit 105. In particular, the virtual reality software system 100 may further include a set of instructions 107. The instructions 107 may detail functional relationships in relation to the structure of the virtual reality software system 100 such that the virtual reality software system 100 can be used, maintained, or the like, in a preferred manner.

Upon reading this specification, it should be appreciated that, under appropriate circumstances, considering such issues as user preferences, design preference, marketing preferences, cost, available materials, technological advances, etc., other virtual reality software system 100 arrangements such as, for example, improvements in the virtual reality headset 110, etc., may be sufficient.

Figure 2:
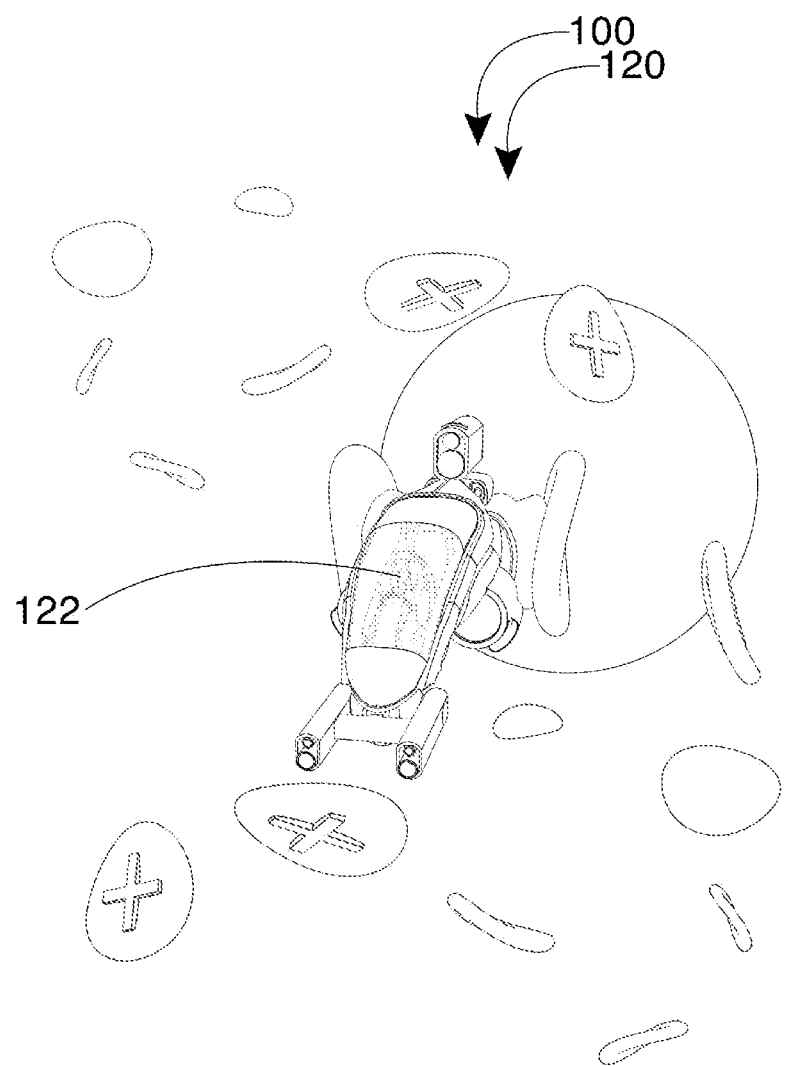
FIG. 2 is an exemplary screen of the virtual reality software system of FIG. 1, according to an embodiment of the present disclosure.

FIG. 2 shows the virtual reality software system 100 of FIG. 1, according to an embodiment of the present disclosure. As above, the virtual reality software system 100 may include the virtual reality headset 110 having the display unit 112 configured to display the three-dimensional virtual reality environment 120. The virtual reality headset 110 includes the processor 114 embedded within. The processor 114 may be configured to provide controls for performing one or more of the multimedia interactions 124 with the three-dimensional virtual reality environment 120. The virtual reality headset 110 further includes the memory 116 removably embedded within. The memory 116 may be configured to store the multimedia interactions 124 made within the three-dimensional virtual reality environment 120. The processor 114 may further be configured to communicate with the memory 116; execute the multimedia interactions 124; and display the multimedia interactions 124 on the display unit 112 such that the user 40 is able to interact with the three-dimensional virtual reality environment 120.

An avatar 122 may be provided with the three-dimensional virtual reality environment 120. This enables the user 40 to virtually interact within the three-dimensional virtual reality environment 120 by use of the multimedia interactions 124. A set of command prompts before beginning the simulation may allow the avatar 122 to be personalized according to characteristics (i.e., hair color, eyes, body shape) and/or the medical condition of the user 40. The medical condition may comprise of a physical illness (i.e., asthma, cancer, etc.) and associated anxiety disorders developed from having the medical condition. The virtual reality software system 100 may provide a therapeutic outlet for the user 40 suffering from the physical illness with associated anxiety.

The three-dimensional virtual reality environment 120 may be representative of an anatomy. Preferred embodiments may include an organ or a blood stream. As shown in FIG. 2, the three-dimensional virtual reality environment 120 represented as the blood stream may contain visual representations of good/bad blood cells. The bad blood cells may be targeted by the avatar 122. The avatar 122 may include a means of transportation throughout the three-dimensional virtual reality environment 120. The three-dimensional virtual reality environment 120 may be customized (or selected) according to the medical condition of the user 40. Customization of the three-dimensional virtual reality environment 120 may occur on the software 150 prior to uploading to the memory 116.

In one embodiment, the medical-mission may comprise of reaching a location within the anatomy and eliminating the virtual-representation(s) of the medical condition. A weapon system may be used for eliminating the virtual-representation(s). The weapon system can be chosen by the user 40.

Figure 3:
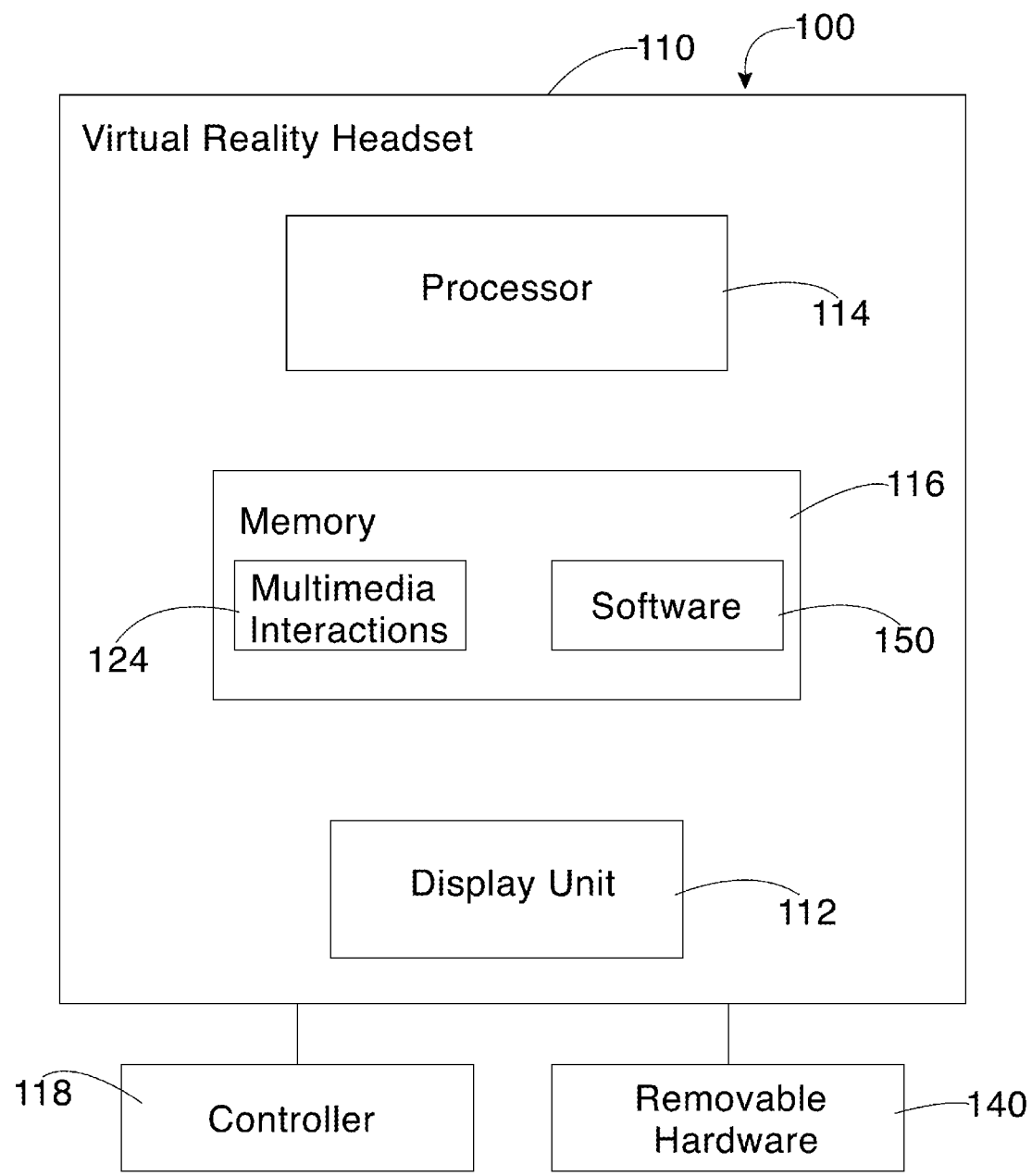
FIG. 3 is a block diagram of the virtual reality software system of FIG. 1, according to an embodiment of the present disclosure.

FIG. 3 is a block diagram of the virtual reality software system 100 of FIG. 1, according to an embodiment of the present disclosure. The virtual reality software system 100 may include the virtual reality headset 110 having the display unit 112 configured to display the three-dimensional virtual reality environment 120. The virtual reality headset 110 includes the processor 114 embedded within. The processor 114 may be configured to provide controls for performing one or more of the multimedia interactions 124 with the three-dimensional virtual reality environment 120. The virtual reality headset 110 further includes the memory 116 removably embedded within. The memory 116 may be configured to store the multimedia interactions 124 made within the three-dimensional virtual reality environment 120. The memory 116 may further be configured to store the software 150. The memory 116 may include the removable hardware 140.

The multimedia interactions 124 may be configured to impart at least one sensory output selected from three-dimensional graphic visuals and audio. To provide the audio, the virtual reality headset 110 may be in communication (wireless or wired) with an auditory output device 130 (i.e., speakers, headphones, or any other known device in the art).

The controller 118 may be in wired or wireless communication with the virtual reality headset 110 and configured to provide controls for performing the multimedia interactions 124. In another embodiment, the controller 118 may be contemplated as the voice recognition system to provide hands-free control over the virtual reality software system 100.

Figure 4:
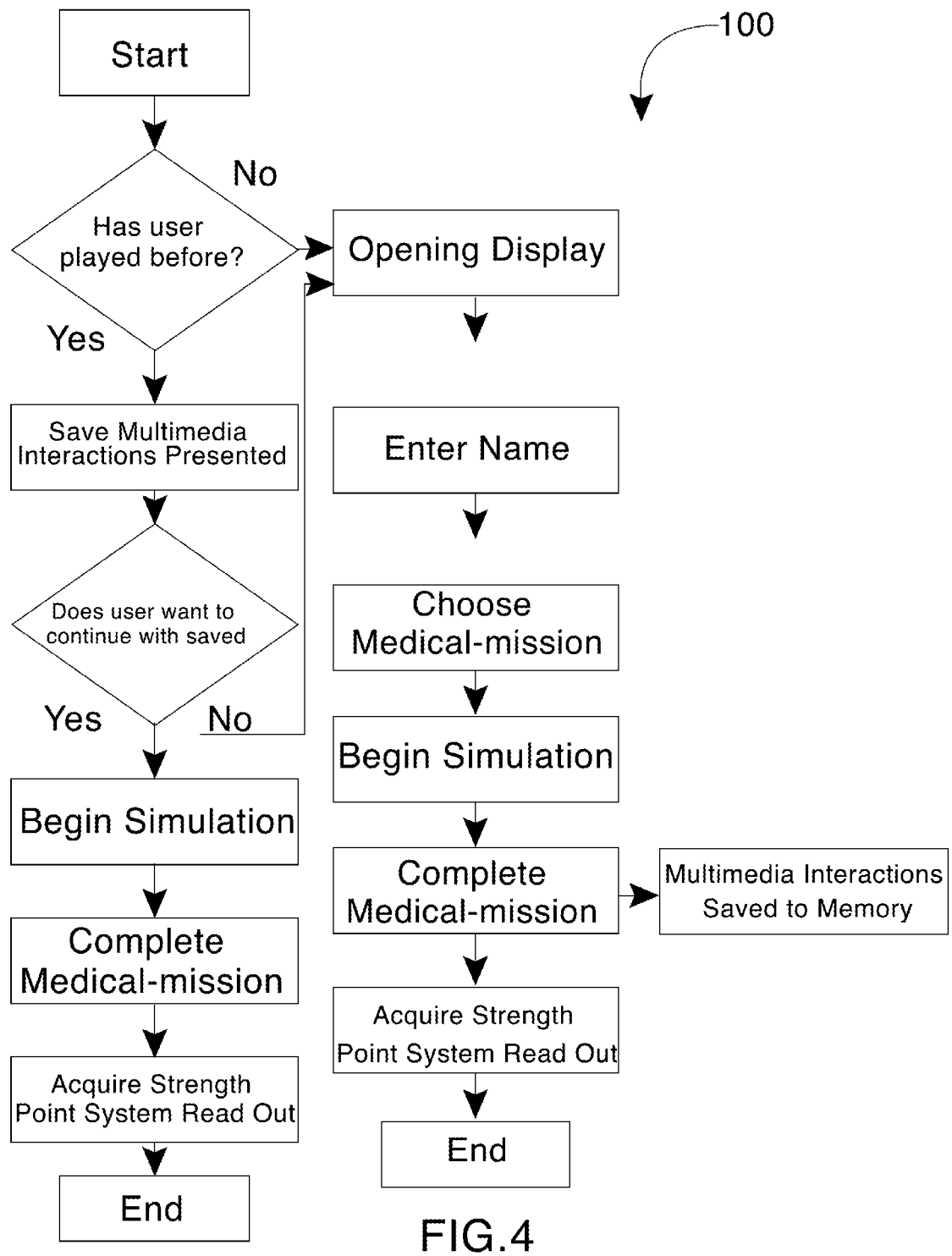
FIG. 4 is a flow diagram of the virtual reality software system of FIG. 1, according to an embodiment of the present disclosure.

FIG. 4 is a flow diagram of the virtual reality software system of FIG. 1, according to an embodiment of the present disclosure. The flow diagram details the steps taken by the user 40 in regard to beginning the simulation and completing the medical-mission. The memory 116 may enable progress of the user 40 to be saved and returned to later. When the medical-mission is complete, a strength point system read out may be acquired. The strength point system read out may provide a performance summary to the user 40.

Figure 5A:
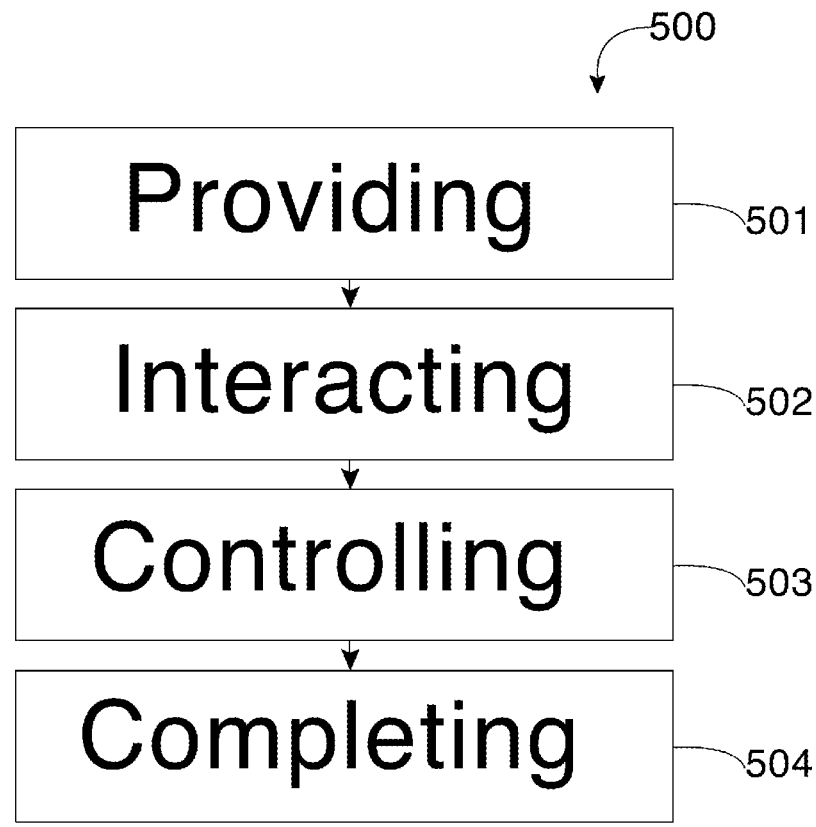
FIG. 5A is a flow diagram illustrating a method using a virtual reality software system, according to an embodiment of the present disclosure.
Figure 5B:
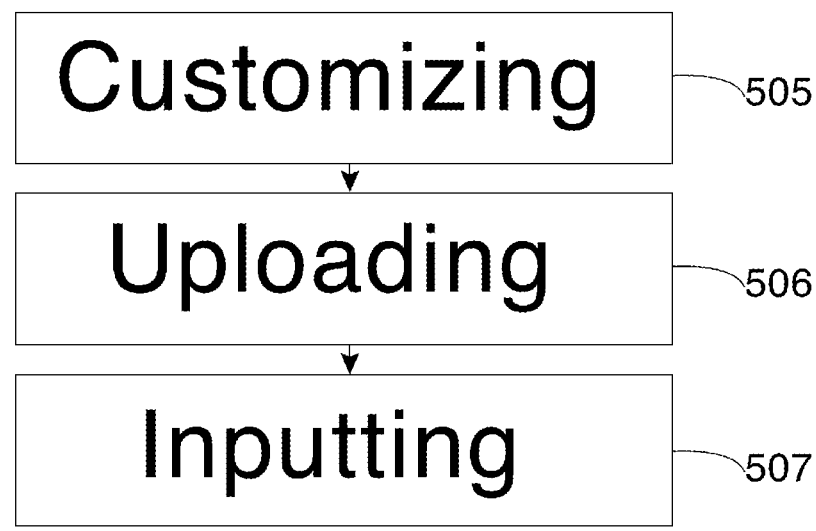
FIG. 5B is a flow diagram illustrating a method using a virtual reality software system, according to an embodiment of the present disclosure.

FIGS. 5A and 5B are flow diagrams illustrating a method for using a virtual reality software system 500, according to an embodiment of the present disclosure. In particular, the method for using the virtual reality software system 500 may include one or more components or features of the virtual reality software system 100 as described above. As illustrated, the method for using the virtual reality software system 500 may include the steps of: step one 501, providing a virtual reality software system 100 comprising a virtual reality headset 110 hosting a software 150 and having a display unit 112 configured to display a three-dimensional virtual reality environment 120, the virtual reality headset 110 including, a processor 114 embedded in the virtual reality headset 110 and configured to provide controls for performing one or more multimedia interactions 124 with the three-dimensional virtual reality environment 120, and a memory 116 removably embedded in the virtual reality headset 110; step two 502, interacting with the three-dimensional virtual reality environment 120 with an avatar 122; step three 503, controlling the avatar 122 via a controller 118 in communication with the virtual reality headset 110; and step four 504, completing a medical-mission with the avatar 122 to provide therapeutic relief to a user 40 for a medical-condition.

The method for using the virtual reality software system may further include the steps of: step five 505, customizing the three-dimensional virtual reality environment 120 on the software 150 to correspond with the medical condition; step six 506, uploading the software 150 to the memory 116, wherein the memory 116 includes a removable hardware 140; and step seven 507, inputting the removable hardware 140 into a port 142 in the virtual reality headset 110, such that the virtual reality headset 110 is able to host the software 150.

It should be noted that the steps described in the method of use 500 can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for the virtual reality software system 100 (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A virtual reality software system for treating a medical condition in a user to improve mental wellbeing and psychological reactions after being diagnosed with the medical condition, the system comprising:
   a virtual reality headset configured to be worn by the user having a display unit configured to display a three-dimensional virtual reality environment, said virtual reality headset including,
      a processor embedded in said virtual reality headset and configured to provide controls for performing one or more multimedia interactions with said three-dimensional virtual reality environment, and
      a memory removably embedded in said virtual reality headset and configured to store said multimedia interactions;
   wherein said processor is further configured to communicate with said memory, to execute said multimedia interactions, and to display said multimedia interactions on said display unit such that said user is able to interact with said three-dimensional virtual reality environment;

wherein said virtual reality headset is configured to host a software providing said three-dimensional virtual reality environment;

an avatar representing the user and enabling the user to virtually interact with the three-dimensional virtual reality environment;

wherein said three-dimensional virtual reality environment is configured to provide a simulation for completing a medical-mission, wherein the medical mission comprises a virtual-representation of the medical condition associated with the user and requires the user to eliminate the virtual-representation of the medical condition by controlling the avatar;

wherein said three-dimensional virtual reality environment is representative of an anatomy;

wherein said medical mission comprises the avatar having a transportation vehicle for traveling to a location within the anatomy and eliminating the virtual representations of the medical condition.

2. The virtual reality software system of claim 1, further comprising a controller in communication with said virtual reality headset and configured to provide controls for performing said multimedia interactions within said three-dimensional virtual environment.

3. The virtual reality software system of claim 1, wherein said virtual reality headset further includes a microphone to provide a voice recognition system permitting said user to perform said multimedia interactions with said three-dimensional virtual environment.

4. The virtual reality software system of claim 1, wherein said avatar is personalized according to characteristics and said medical condition of said user.

5. The virtual reality software system of claim 1, wherein said medical condition comprises a physical illness.

6. The virtual reality software system of claim 5, wherein said medical condition comprises anxiety disorders associated with said physical illness.

7. The virtual reality software system of claim 1, wherein said multimedia interactions are configured to impart at least one sensory output selected from three-dimensional graphic visuals and audio.

8. The virtual reality software system of claim 7, wherein said virtual reality headset is in communication with an auditory output device for providing said audio to said user.

9. The virtual reality software system of claim 1, wherein said memory is further configured to store said software.

10. The virtual reality software system of claim 1, wherein said memory includes removable hardware.

11. The virtual reality software system of claim 10, wherein said removable hardware is a flash memory card.

12. The virtual reality software system of claim 11, wherein said virtual reality headset includes a port for receiving said hardware.

13. The virtual reality software system of claim 1, further comprising a weapons system accessible by the avatar, wherein the weapons system is adapted to allow the user to destroy the medical condition via a weapon from the weapons system.

14. The virtual reality software system of claim 1, further comprising a strength point system that provides a performance summary to the user when the medical mission is completed.

15. The virtual reality software system of claim 1, wherein the anatomy is a blood stream and the virtual-representation of the medical condition comprises blood cells within the blood stream.

16. A virtual reality software system for treating a medical condition in a user to improve mental wellbeing and psychological reactions after being diagnosed with the medical condition, the virtual reality software system comprising:

a virtual reality headset having a display unit configured to display a three-dimensional virtual reality environment, said virtual reality headset including, a processor embedded in said virtual reality headset and configured to provide controls for performing one or more multimedia interactions with said three-dimensional virtual reality environment, and a memory removably embedded in said virtual reality headset and configured to store said multimedia interactions;

wherein said processor is further configured
to communicate with said memory,
to execute said multimedia interactions, and
to display said multimedia interactions on said display unit such that said user is able to interact with said three-dimensional virtual reality environment;

wherein said virtual reality headset is configured to host a software providing said three- dimensional virtual reality environment;

wherein said three-dimensional virtual reality environment is configured to provide a simulation for completing a medical-mission to eliminate a virtual-representation of a medical condition associated with said user;

further comprising a controller in communication with said virtual reality headset and configured to provide controls for performing said multimedia interactions within said three-dimensional virtual environment;

wherein said virtual reality headset further includes a microphone to provide a voice recognition system permitting said user to perform said multimedia interactions with said three-dimensional virtual environment;

further comprising an avatar enabling said user to virtually interact with said three-dimensional virtual reality environment;

the avatar representing the user and enabling said user to virtually interact with said three- dimensional virtual reality environment;

wherein said three-dimensional virtual reality environment is configured to provide a simulation for completing a medical-mission, wherein the medical mission comprises a virtual- representation of the medical condition associated with the user and requires the user to eliminate the virtual-representation of the medical condition by controlling the avatar associated with said user;

wherein said three-dimensional virtual reality environment is representative of an anatomy;

wherein said medical mission comprises the avatar having a transportation vehicle for traveling to a location within the anatomy and eliminating the virtual representations of the medical condition;

wherein said avatar is personalized according to characteristics and said medical condition of said user;

wherein said medical condition comprises a physical illness;

wherein said three-dimensional virtual reality environment is representative of an anatomy;

wherein said medical-mission comprises of reaching a location within said anatomy and eliminating said virtual-representation(s) of said medical condition;

wherein said three-dimensional virtual reality environment is customized according to said medical condition of said user;

wherein said multimedia interactions are configured to impart at least one sensory output selected from three-dimensional graphic visuals and audio;

wherein said virtual reality headset is in communication with an auditory output device for providing said audio to said user;

wherein said memory is further configured to store said software;

wherein said memory includes removable hardware; and wherein said removable hardware is a flash memory card.

17. A method for using a virtual reality software system, the method comprising the steps of:

providing a virtual reality software system comprising:

a virtual reality headset hosting a software and having a display unit configured to display a three- dimensional virtual reality environment said virtual reality headset including, a processor embedded in said virtual reality headset and configured to provide controls for performing one or more multimedia interactions with said three-dimensional virtual reality environment, and a memory removably embedded in said virtual reality headset, interacting with said three-dimensional virtual reality environment with an avatar, the avatar representing the user and enabling said user to virtually interact with said three-dimensional virtual reality environment, wherein said three-dimensional virtual reality environment is configured to provide a simulation for completing a medical-mission, wherein the medical mission comprises a virtual-representation of the medical condition the user and requires the user to eliminate the virtual- representation of the medical condition by controlling the avatar associated with said user;

wherein said three-dimensional virtual reality environment is representative of an anatomy;

wherein said medical mission comprises the avatar having a transportation vehicle for traveling to a location within the anatomy and eliminating the virtual representations of the medical condition;

controlling said avatar via a controller in communication with said virtual reality headset, and completing the medical-mission with said avatar to provide therapeutic relief to a user for a medical-condition.

18. The method of claim 17, further comprising the steps of:

customizing said three-dimensional virtual reality environment on said software to correspond with said medical condition;

uploading said software to said memory, wherein said memory includes a removeable hardware; and inputting said removeable hardware into a port in said virtual reality headset, such that said virtual reality headset is able to host said software.

\* \* \* \* \*